US010697983B2

(12) United States Patent
Rahane et al.

(10) Patent No.: US 10,697,983 B2
(45) Date of Patent: *Jun. 30, 2020

(54) METHODS OF EVALUATING QUALITY OF MEDIA SUITABLE FOR REMOVING ANTI-A OR ANTI-B ANTIBODIES

(71) Applicant: Merck Patent GmbH, Darmstadt (DE)

(72) Inventors: Santosh Rahane, Acton, MA (US); Matthew Turiano, Westford, MA (US); Nanying Bian, Lexington, MA (US); Matthew T. Stone, Arlington, MA (US)

(73) Assignee: Merck Patent GmbH, Darmstadt (DE)

( * ) Notice: Subject to any disclaimer, the term of this patent is extended or adjusted under 35 U.S.C. 154(b) by 647 days.

This patent is subject to a terminal disclaimer.

(21) Appl. No.: 15/226,441

(22) Filed: Aug. 2, 2016

(65) Prior Publication Data

US 2017/0067915 A1 Mar. 9, 2017

Related U.S. Application Data

(60) Provisional application No. 62/215,431, filed on Sep. 8, 2015.

(51) Int. Cl.

| | | |
|---|---|---|
| *G01N 33/80* | (2006.01) | |
| *B01D 15/38* | (2006.01) | |
| *G01N 30/88* | (2006.01) | |
| *G01N 30/50* | (2006.01) | |
| *B01D 15/20* | (2006.01) | |
| *C07K 1/22* | (2006.01) | |
| *G01N 30/02* | (2006.01) | |

(52) U.S. Cl.
CPC .............. *G01N 33/80* (2013.01); *B01D 15/20* (2013.01); *B01D 15/3809* (2013.01); *C07K 1/22* (2013.01); *G01N 30/50* (2013.01); *G01N 30/88* (2013.01); *G01N 2030/027* (2013.01); *G01N 2030/889* (2013.01)

(58) Field of Classification Search
None
See application file for complete search history.

(56) References Cited

U.S. PATENT DOCUMENTS

| | | |
|---|---|---|
| 4,137,401 A | 1/1979 | Lemieux et al. |
| 4,195,174 A | 3/1980 | Lemieux et al. |
| 4,362,720 A | 12/1982 | Lemieux et al. |
| 4,404,188 A | 9/1983 | Donahoe et al. |
| 4,664,913 A | 5/1987 | Mielke et al. |
| 5,149,425 A | 9/1992 | Mazid |
| 5,541,294 A | 7/1996 | Horowitz et al. |
| 8,153,382 B2 | 4/2012 | Chtourou et al. |
| 2006/0073534 A1 | 4/2006 | Kelly et al. |
| 2009/0074749 A1 | 3/2009 | Chtourou et al. |
| 2010/0181254 A1 | 7/2010 | Graalfs |
| 2012/0039886 A1 | 2/2012 | Elzaabi |
| 2013/0046056 A1 | 2/2013 | Spector et al. |
| 2015/0111194 A1 | 4/2015 | Rempfer et al. |

FOREIGN PATENT DOCUMENTS

| | | |
|---|---|---|
| CA | 2385179 A1 | 4/2001 |
| CN | 1276527 A | 12/2000 |
| CN | 101678318 A | 3/2010 |
| CN | 103394084 A | 11/2013 |
| CN | 104053462 A | 9/2014 |
| EP | 0488755 A1 | 6/1992 |
| EP | 1224462 A2 | 7/2002 |
| EP | 1451589 A2 | 9/2004 |
| EP | 2202310 A2 | 6/2010 |
| EP | 2358391 B1 | 12/2014 |
| FR | 3008097 A1 | 1/2015 |
| FR | 3008098 A1 | 1/2015 |
| JP | 4-203967 A | 7/1992 |
| JP | 07-242698 A | 9/1995 |
| JP | 2003-511468 A | 3/2003 |
| JP | 2009-521520 A | 6/2009 |
| JP | 2010-528271 A | 8/2010 |
| JP | 2012-229212 A | 11/2012 |
| JP | 2012-254981 A | 12/2012 |
| JP | 2013-151507 A | 8/2013 |
| JP | 2014-531966 A | 12/2014 |
| KR | 10-1207797 B1 | 11/2012 |
| WO | 2001/27623 A2 | 4/2001 |
| WO | 2003/043403 A2 | 5/2003 |
| WO | 2009/154375 A2 | 12/2009 |
| WO | 2010/076496 A1 | 7/2010 |
| WO | 2013/062479 A1 | 5/2013 |
| WO | 2015/001277 A1 | 1/2015 |
| WO | 2015/034566 A1 | 3/2015 |
| WO | 2015/049651 A1 | 4/2015 |

OTHER PUBLICATIONS

Extended European Search Report received for European Patent Application No. 16187836.8, dated Feb. 1, 2017, 10 pages.
Extended European Search Report received for European Patent Application No. 16187837.6, dated Feb. 1, 2017, 9 pages.
Extended European Search Report received for European Patent Application No. 16187838.4, dated Jan. 31, 2017, 8 pages.
Rogers et al.,"Development of a Rapid Sanitization Solution for Silica-Based Protein A Affinity Adsorbents", Journal of Chromatography A, vol. 1216, Issue 21, Mar. 28, 2009, pp. 4589-4596.
Schulte et al.,"Comparative Affinity Chromatographic Studies Using Novel Grafted Polyamide and Poly(vinyl alcohol) media", Journal of Chromatography, vol. 539, Issue 2, 1991, pp. 307-314.
Tu et al.,"Preparation and Characterization of Novel IgG Affinity Resin Coupling Anti-Fc Camelid Single-Domain Antibodies", Journal of Chromatography B: Biomedical Sciences & Applications, vol. 983-984, Jan. 14, 2015, pp. 26-31.
Solovan et al., "Synthetic Blood Group Antigens for Anti-A Removal Device and Their Interaction With Monoclonal Anti-A IgM", Transplant Immunology, vol. 16, Dec. 31, 2006, pp. 245-249.

(Continued)

*Primary Examiner* — Joseph Woitach
(74) *Attorney, Agent, or Firm* — EMD Millipore Corporation (57) ABSTRACT

Embodiments described herein relate to methods of evaluating quality of a chromatography media for removal of anti-A or anti-B antibodies from a sample, where the methods employ use of purified Lectins.

23 Claims, 1 Drawing Sheet

(56) References Cited

OTHER PUBLICATIONS

Alikhani et al.,"High Molecular Weight Blood Group A Trisaccharide-Polyacrylamide Glycoconjugates as Synthetic Blood Group A Antigens for Anti-A Antibody Removal Devices",Journal of Biomedical Materials Research Part B: Applied Biomaterials, vol. 91, 2009, pp. 845-854.
Bensinger et al.,"Immunoadsorption for Removal of A and B Blood-Group Antibodies", New England Journal of Medicine, vol. 304, Issue 3, Jan. 15, 1981, pp. 160-162.
Bensinger et al.,"In Vitro and In Vivo Removal of Anti-A Erythrocyte Antibody by Adsorption to a Synthetic Immunoadsorbent", Transfusion, vol. 21, Issue 3, May-Jun. 1981, pp. 335-342.
Bensinger et al.,"Whole Blood Immunoadsorption of Anti-A or Anti-B Antibodies", Vox Sanguinis, vol. 48, Issue 6, Jun. 1985, pp. 357-361.
Blomberg et al.,"Improved Removal of Anti-A and Anti-B Antibodies from Plasma Using Blood-Group-Active Haptens", Vox Sanguinis, vol. 65, Issue 2, Jul. 1993, pp. 126-135.
Dhainaut et al.,"In Vitro and In Vivo Properties Differ Among Liquid Intravenous Immunoglobulin Preparations", Vox Sanguinis; vol. 104, Issue 2, Feb. 2013, pp. 115-126.
Gautam et al.,"Monoclonal Anti-A Antibody Removal by Synthetic A Antigen Immobilized on Specific Antibody Filters",Biotechnology and Bioengineering, vol. 99, No. 4, Mar. 1, 2008, pp. 876-883.
McDonald et al.,"A New Monoclonal Anti-A Antibody BIRMA-1: A Potent Culture Supernatant Which Agglutinates Ax Cells, but Does Not Give Undesirable Reactions with B Cells", Vox Sanguinis, vol. 61, 1991, pp. 53-58.
Rieben et al.,"In Vitro Evaluation of the Efficacy and Biocompatibility of New, Synthetic ABO Immunoabsorbents", Transplantation, vol. 60, Issue 5, Sep. 15, 1995, pp. 425-430.
Rydberg et al., "Characterisation of the Anti-A Antibody Response Following an ABO Incompatible (A2 to O) Kidney Transplantation",Molecular Immunology, vol. 29, Issue 4, Apr. 1992, pp. 547-560.
Rydberg et al.,"In Vitro Assessment of a New ABO Immunosorbent With Synthetic Carbohydrates Attached to Sepharose", Transplant International, vol. 17, Issue 11, Jan. 2005, pp. 666-672.
Thorpe et al.,"International Collaborative Study to Evaluate Candidate Reference Reagents to Standardize Haemagglutination Testing for Anti-A and Anti-B in Normal intravenous immunoglobulin products", Vox Sanguinis, vol. 97, 2009, pp. 160-168.
"Strategies to Address Hemolytic Complications of Immune Globulin Infusions", FDA, Centre for Biologics Evaluation and Research, Center for Drug Evaluation and Research, Workshop on Risk Mitigation Measure Strategies, Jan. 28, 2014, 348 pages.
Christensson et al., "Flow Cytometric Quantitation of Serum Anti-D in Pregnancy", Transfusion, vol. 36, Issue 6, Jun. 1996, pp. 500-505.
Crawford et al., "Practical Application of Synthetic A and B Blood Group Immunoadsorbents", Blood Transfusion and Immunohaematology, vol. 24, Issue 3, 1981, pp. 281-287.
Lemieux, R.U., "Human Blood Groups and Carbohydrate Chemistry", Haworth Memorial Lecture, Chemical Society Reviews, 1978, vol. 7, pp. 423-452.
Lockyer et al., "Absorption of Unwanted Anti-A-B Agglutinins from Anti-Rh D Grouping Sera Using Time-Expired Formalised Heat-Treated A1 B Rh D Positive Red Cells", Vox Sanguinis, vol. 12, Issue 1, Jan. 1967, pp. 75-77.
Matsui et al., "Comparative Study of Blood Group-Recognizing Lectins toward ABO Blood Group Antigens on Neoglycoproteins, Glycoproteins and Complex-Type Oligosaccharides", Biochimica et Biophysica Acta (BBA), vol. 1525, Issues 1-2, Feb. 16, 2001, pp. 50-57.
Oyen et al., "Use of *Escherichia coli* O86: B7 in the Adsorption of Anti-A and Anti-B from Blood Typing Sera", Transfusion, vol. 12, Issue 2, Mar. 4, 1972 , pp. 98-102.
Sharon et al., "Lectins", Second Edition, Springer Publications, 2007, 4 pages.

Figure 1

Figure 2

METHODS OF EVALUATING QUALITY OF MEDIA SUITABLE FOR REMOVING ANTI-A OR ANTI-B ANTIBODIES

CROSS-REFERENCED TO RELATED APPLICATIONS

The present application claims the benefit of priority of U.S. Provisional Patent Application No. 62/215,431, filing date Sep. 8, 2015, the entire content of which is incorporated herein in its entirety.

BACKGROUND

Human plasma enriched in immunoglobulins is used for the treatment of many disorders as well as to treat certain congenital deficiencies. Typically, human plasma is obtained by pooling the plasma from multiple donors, having different blood group types. Blood group types may be divided into 4 major types. Blood group type A—having only the A antigen on red cells (and B antibody in the plasma); blood group type B—having only the B antigen on red cells (and A antibody in the plasma); blood group type AB—having both A and B antigens on red cells (but neither A nor B antibody in the plasma); and blood group type O—having neither A nor B antigens on red cells (but both A and B antibodies are in the plasma).

It is important that the red bloods cells of a person having a particular blood group type antigen, such as A, never come in contact with the antibodies that will bind to this antigen, such as anti-A antibodies, because contact with such antibodies would result in agglutination and/or hemolysis of their red blood cells that can even result in death. Therefore, a recipient having blood group type A may only receive plasma from a donor having blood group type A or blood group type AB; a recipient having blood group type B may only receive plasma from a donor having blood group type B or blood group type AB; a recipient having blood group AB may only receive plasma from a donor having blood group type AB; and a recipient having blood group type O is deemed a universal recipient. Compatibility of the different blood group types is important for the development of safe blood transfusions and organ transplants. However, in case of blood derived therapeutic drugs that rely on pooling of blood plasma from a large numbers of people, it becomes particularly challenging to ensure that a recipient does not receive non-compatible plasma.

A number of approaches have been developed to selectively remove blood group type antibodies from plasma, including formalinized heat-treated red cells (Vox Sang., 1967, 12, 75-77), heat treated *Escherichia coli* $O_{86}$:B7 having A and B antigens (Transfusion, 1972, 12, 98-102), red cell stroma powder, red cell stroma antigen derived immunoadsorbents (Chemical Soc. Rev., 1978, 7, 423-452), and synthetic blood group A and B immunoadsorbents (Rev. Fr. Transfus. Immunohematol. 1981, 24, 3, 281-287).

Solid phase chromatography immunoadsorbents have been developed as commercial chromatography media for the treatment of blood derived products and also for the preparation of donors before transplantation to an ABO incompatible recipient. One of the key advantages of employing synthetic immunoadsorbents is that they are synthetically constructed instead of being derived from natural sources and therefore have more consistent properties from batch to batch.

Currently, some of the commercially available chromatographic media with blood group A antigen (A-antigen) ligands and/or blood group B antigen (B-antigen) ligands include the Glycosorb-ABO device (Glycorex Transplantation AB). This Glycosorb device is used to prepare organ donors for transplantation to patients having incompatible blood types. The blood group antigen ligands in the Glycosorb-ABO device bind and remove the blood group A antigen antibodies (anti-A) and blood group B antigen antibodies (anti-B) from the blood of organ donors thus reducing the risk of organ rejection.

One of the major challenges in utilizing chromatography media for the purification of blood derived products is the lack of an efficient and reproducible method to evaluate the relative quality of different media, e.g., different batches of same type of media or media from different sources or the same media samples over time.

SUMMARY

Embodiments described herein relate to methods of assessing quality of a chromatography media containing blood group A antigen ligand or blood group B antigen ligand. Methods described herein are especially useful for assessing or evaluating quality of same type of media from batch to batch, during and after use and for optimizing the media during development.

In some embodiments, a method for comparing quality of two or more affinity chromatography media samples is provided, both containing blood group A antigen ligands attached to a solid support, where the method comprises the steps of: (a) providing two or more affinity chromatography media samples, each of volume VR; (b) incubating each sample with a solution of purified *Helix Pomatia* (HP) Lectin of known concentration C1 and volume VM; (c) obtaining a supernatant for each of the samples and measuring the concentration C2 of the purified HP Lectin in each supernatant; determining the static binding capacity of each of the affinity chromatography media samples using the following equation.

$$\frac{[C1 - C2] \times VM}{VR}$$

wherein the static binding capacities of the media samples for HP Lectin correlates with their ability to remove anti-A antibodies from a sample, thereby providing a comparison of the quality of the two or more different affinity chromatography media samples.

In other embodiments, a method for comparing quality of two or more affinity chromatography media samples is provided, each containing blood group B antigen ligands attached to a solid support, where the method comprises the steps of: (a) providing two or more affinity chromatography media samples, each of volume VR; (b) incubating each sample with a solution of purified *Griffonia simplicifolia*—IsoLectin B4 (GSI-B4) Lectin of known concentration C1 and volume VM; (c) obtaining a supernatant for each of the samples and measuring the concentration C2 of purified GSI-B4 Lectin in each supernatant; determining the static binding capacity of each of the affinity chromatography media samples using the following equation.

$$\frac{[C1 - C2] \times VM}{VR}$$

wherein the static binding capacities of the media samples for—purified GSI-B4 Lectin correlates with their ability to remove anti-B antibodies from a sample, thereby providing a comparison of the quality of two or more affinity chromatography media samples.

A media sample having higher binding capacity for HP Lectin or GSI-B4 Lectin, relative to other samples it is compared with, is of better quality compared to the other media samples.

In some embodiments according to the methods described herein, the solid support is a porous or non-porous polymeric solid support comprising a polymer selected from the group consisting of polyvinylether, polyvinylalcohol, polymethacrylate, polyacrylate, polystyrene, polyacrylamide, polymethacrylamide and polycarbonate. In a particular embodiment, the solid support is a polyvinylether based solid support. In some embodiments, the solid support is in bead form (e.g., a polyvinyl ether based bead).

In some embodiments described herein, the different affinity chromatography media samples constitutes different batches of the same type of media.

In other embodiments, the different affinity chromatography media samples constitute the same media at different stages of use.

In some embodiments, the media are capable of removing anti-A or anti-B antibodies from a sample selected from the group consisting of blood, blood products, plasma, plasma derivatives and IVIG feed.

In some embodiments, the concentration of HP Lectin or GSI-B4 Lectin in supernatant is measured using absorbance at 280 nm.

Also provided herein are methods of assessing quality of an affinity chromatography media containing blood group A antigen ligand or blood group B antigen ligand attached to a solid support, following exposure of the affinity chromatography media to acid or alkaline conditions, the method comprising the steps of: (a) providing a chromatography media having either blood group A antigen ligands or blood group B antigen ligands attached to a solid support; (b) measuring the binding capacity of the media for a purified HP Lectin in case of blood group A antigen ligand media or for a purified GSI-B4 Lectin in case of blood group B antigen ligand media; (c) exposing the media to acid or alkaline conditions for at least 5 hours; and (d) measuring the binding capacity of the media for purified HP Lectin in case of blood group A antigen ligand media or for purified GSI-B4 Lectin in case of blood group B antigen ligand media; wherein a reduction in the binding capacity of media in step (d) relative to step (b) indicates that the quality of media has reduced following exposure to acid of alkaline conditions.

The embodiments described herein can also be used for determining whether a media comprises blood group A antigen ligands or blood group B antigen ligands, where the method comprises the steps of: (a) providing a media, where it is unknown whether the media comprises blood group A antigen ligands or blood group B antigen ligands; (b) measuring the binding capacity of the unknown media for purified HP Lectin and separately for purified GSI-B4 Lectin; and (c) comparing the capacity of the unknown media for purified HP Lectin and purified GSI-B4 Lectin; where the unknown media is determined to comprise blood group A antigen ligands, if it has a higher binding capacity for HP Lectin relative to binding capacity for GSI-B4 Lectin, and the unknown media is determined to comprise blood group B antigen ligands if it has a higher binding capacity for GSI-B4 Lectin relative to binding capacity for HP Lectin.

DETAILED DESCRIPTION

Recently there has been an increased interest in the application of synthetic immunoadsorbent chromatography media for the removal of anti-A and anti-B IgG from intravenous immunoglobulin (IVIG), which consists of concentrated polyvalent IgG antibodies extracted from pooled plasma obtained from several blood donors, sometimes as many as thousand or greater than thousand blood donors. During the process of purifying the IgG from blood plasma, the larger anti-A and anti-B IgM antibodies can typically be separated from the smaller IgG antibodies by fractionation. However, some percentage of the anti-A and anti-B antibodies are generally in the form of IgG that cannot be distinguished from the other IgG antibodies by fractionation alone. Thus, IVIG therapeutic concentrates are typically screened using an agglutination assay to monitor the concentrations of anti-A and anti-B IgG antibodies in order to prevent administration of IVIG with high concentrations of anti-A and anti-B IgG antibodies. However, despite this precaution, hemolytic reactions that can lead to death, are still known to occur for those recipients having blood group types A, B, or AB (Transcript for "Strategies to address hemolytic complications of immune globulin infusions," FDA Center for Biologics Evaluation and Research Public Workshop Washington, D.C. Jan. 28-29, 2014).

Common agglutination assays rely on the use of live red blood cells, which have limited lifetimes and the density of antigens on the cell surface generally vary from lot to lot. Agglutination also requires serial dilutions and relies on a qualitative evaluation (visual or microscopic observations) of cell agglutination. A more accurate method to determine the concentrations of anti-A and anti-B antibodies employs flow-cytometry. However, flow-cytometry methods also use live red blood cells and are significantly more complex and time consuming than agglutination assays. ELISA assays have also been reported to measure the concentration of anti-A and anti-B antibodies, however this technique requires a relatively complex multistep procedure and specialized antigen reagents.

As discussed above, chromatography immunoadsorbent media containing ligands that bind anti-A or anti-B antibodies are considered effective for the removal of such antibodies from blood derived products, e.g., plasma and IVIG. However, currently, there are no good methods available which may be used for qualification and validation of such media, in order to assess their reproducibility and reliability.

It is especially important to evaluate the batch-to-batch quality of blood group antigen ligand chromatography media in order to ensure that the media meets production specifications and quality requirements throughout its lifetime. Further, it is also important to evaluate such media during and after use, cleaning and sanitization to make sure that it retains the ability to remove the intended impurities following use, cleaning and sanitization procedures. The ability of blood group antigen ligand media to bind their intended target molecules has usually been evaluated directly by measuring the reduction in the concentration of polyclonal blood group antigen antibodies in blood derived products before and after contact with the blood group antigen ligand media.

As evidenced by the Examples herein, the capacity of anti-A and anti-B antigen ligand media for certain purified Lectins correlates with the ability of such media to remove anti-A antibodies or anti-B antibodies, as the case maybe, from a sample (e.g., an IVIG feed).

Measuring the capacity of the blood group antigen ligand containing media for a purified molecule (e.g., a purified Lectin in this case) has several advantages over previously described methods, which largely relied on measuring the removal of blood group antigen antibodies from blood products, which is both time consuming and difficult to reproduce. In contrast, the embodiments described herein rely on measuring the binding capacity for a purified molecule that can be performed more efficiently and reproducibly compared to the conventional methods known in the art.

Embodiments described herein relate to a new method for evaluating the quality of blood group antigen ligand media that can be performed more efficiently and reproducibly compared to the conventional methods known in the art. The methods described herein have several advantages over conventional methods known in the art. For example, not only are the methods described herein more efficient, straight forward and readily reproducible compared to most commonly used agglutination based assays, but the methods described herein do not require any specialized equipment (e.g., for flow-cytometry) or any specialized blood group antigen reagents (e.g., for ELISA based assays).

As evidenced by the Examples herein, the capacity of anti-A and anti-B antigen ligand media for a purified Lectin correlates with the ability of the media to remove blood group A antibodies or blood group B antibodies, as the case maybe, from an IVIG feed. The methods provided herein rely on measuring the binding capacity of such media for purified Lectins and are easy to perform, take less time and are far more reliable and reproducible than existing methods known in the art.

Measuring the binding capacity of blood group antigen media for purified Lectins has several advantages over existing methods. For example, as compared to agglutination, which relies on live red blood cells that tend to show a lot of variability from lot to lot and also on operator's subjective observations of agglutination, the use of purified Lectins greatly reduces or eliminates errors and also provides consistent results.

Lectins are naturally occurring carbohydrate-binding proteins that are capable of agglutinating cells. Lectins are known to exhibit specificity for human blood types and cause preferential agglutination of malignant cells at physiological conditions. To-date, approximately 400 Lectins have been identified and extracted from plant and animal sources. [Sharon, N., and Lis, H., *Lectins,* 2nd ed.; Springer Publications, The Netherlands, 2007.]

It has been previously reported that several Lectins including Lectins from *Griffonia simplicifolia* (GS-I), *Griffonia simplicifolia*—IsoLectin B4 (GSI-B4), and *Helix Pomatia* (HP), exhibit binding specificity for blood group antigens. [Matsui, T. et al, *Biochim. et. Biophys. Acta,* 1525, 2001, 50-57].

Table 1 summarizes the Lectins, their sources along with the specificities towards blood group antigens.

TABLE 1

Blood group specific Lectins, Sources, and Blood Group Specificities

| Lectin | Species of Origin | Blood Group Specificity |
|---|---|---|
| *Helix Pomatia* Lectin (HPA) | *Helix pomatia* | A |
| *Dolichos Biflorus* Lectin (DBA) | *Dolichos biflorus* | $A_1 > A_2$ |
| *Vicia Villosa* Lectin (VVA) | *Vicia villosa* | $A_1$ |
| *Phaseolus Lunatus* Lectin (LBA) | *Phaseolus lunatus* | $A_1 > A_2 \gg B$ |
| *Glycine Max* Lectin (SBA) | *Glycine max* | $A_1 > A_2 \gg B$ |
| *Wistarita Floribunda* Lectin (WFA) | *Wistarita floribunda* | A > B, O |
| *Griffinia Simplicifolia*-B4 IsoLectin (GSI-B4) | *Griffonia simplicifolia* | B |
| *Euonymus Europaeus* Lectin (EEA) | *Euonymus europaeus* | B, O ($A_2$) |
| *Sophora Japonica* Lectin (SJA) | *Sophora japonica* | $B > A \gg O$ |
| *Ulex Europaeus* Lectin (UEA-I) | *Ulex europaeus* | O |
| *Lotus Tetragonolobus* Lectin (LTA) | *Lotus tetragonolobus* | O |

While several Lectins are identified as blood group specific, very few are commercially available. For example, it has been reported that the commercially available HP and GSI-B4 Lectins have binding specificity for blood group A antigen and blood group B antigen, respectively. In contrast, GS-I Lectin has been reported to exhibit binding specificity for both blood group antigen A and B. These Lectins are about the same size as monomeric IgG antibodies (~150 kDa) and are expected to exhibit similar mass transfer properties as those of monomeric IgG antibodies; however, they are very different in overall structure and composition.

Despite the inherent differences in the type and the source of the Lectin and IgG molecules, it was observed herein that the static binding capacities of blood group A antigen and blood group B antigen media for certain purified Lectins correlates with their ability to remove anti-A and anti-B antibodies from a sample, e.g., an IVIG feed. The percentage removal of anti-A and anti-B antibodies from an IVIG feed was found to be the highest for those media which had the highest binding capacities for HP and GSI-B4 Lectins, respectively. Notably, measuring the static binding capacity of a media for Lectins is much faster and less complex than the flow-cytometry process that is typically used to measure the reduction in the concentration of anti-A and anti-B antibodies in an IVIG feed.

In order that the embodiments disclosed herein may be more readily understood, certain terms are first defined. Additional definitions are set forth throughout the detailed description.

I. Definitions

The term "binding capacity" refers to the amount of a molecule which binds to a defined volume of media packed in a column and run under defined conditions The binding capacity of a chromatography media described herein is the amount of anti-A or anti-B antibodies that the chromatography media can bind per volume of media at a set flow rate.

In the embodiments described herein, a purified Lectin is used to evaluate the binding capacity of a chromatography media suitable for removing anti-A or anti-B antibodies; and such binding capacity correlates with the ability of such media to remove anti-A or anti-B antibodies. In other words, the binding capacity of a chromatography media for a specific purified Lectin, as described herein, can be used as an indicia to determine the effectiveness of the media to remove anti-A or anti-B antibodies, as the case may be. The binding capacity may be measured as static binding capacity or dynamic binding capacity. In a particular embodiment, static binding capacity of media for certain purified Lectins is measured herein.

The term "static binding capacity" of a media (e.g., a chromatography media) is defined as the amount of a protein bound by the media divided by the volume of the media used. An exemplary method for measuring the static binding capacity of a chromatography media is as follows. After contacting the chromatography media with the protein solution of known concentration, the solution is allowed to incubate with the media to facilitate binding of the protein to the chromatography media. The incubation time may vary (e.g., from 5 minutes to 72 hours) and can be readily determined by one of ordinary skill in the art, e.g., by measuring the concentration of the protein in the supernatant periodically (e.g., by measuring absorbance at 280 nm) until there is no measurable change in the concentration in the supernatant. Once equilibrium is reached between the protein bound to the chromatography media and that in solution, the concentration of the protein solution is once again measured in the supernatant. The static binding capacity is then measured by the starting amount of protein (before incubation) minus the amount of protein in the supernatant (after incubation) divided by the volume of the media used.

The static binding capacity of a particular chromatography media is generally influenced by the composition of the protein solution including one or more of the following factors, e.g., concentration of the protein, amount of chromatographic media used, concentration of other components in the solution (salts, organic molecules, buffers), the solution pH, and conductivity. It may also be influenced by the temperature of the protein solution. All of these variables are generally held constant in order to allow the comparison of static binding capacity between two different chromatography media. The term "static binding capacity" may also be referred to as "saturation binding capacity" or "maximum binding capacity."

In some embodiments described herein, static binding capacity of a blood group A antigen ligand containing media or blood group B antigen ligand containing media for a purified Lectin molecule is used as an indicia to predict or assess its ability to remove anti-A or anti-B antibodies, as the case may be, from a sample (e.g., an IVIG feed). Comparing the static binding capacity of two different batches of media or the same media over time or media from different sources, is especially useful, as it provides information about the quality of the media. In other words, since the binding capacity for a purified Lectin molecule (HP Lectin in case of blood group A antigen ligand media or GSI-B4 Lectin in case of blood group B antigen ligand media) correlates with its ability to remove anti-A or anti-B antibodies, as the case may be, the binding capacity can be used to evaluate and compare the performance of different batches of a media or the same media over time or media from different sources. Accordingly, using the methods described herein, one of ordinary skill or an end user in the art can readily determine whether a batch of media exhibits loss in its performance (i.e., ability to remove anti-A or anti-B antibodies) over another batch of the same type of media, or over time, especially after repeated cleaning and sanitization. Further, measurement of static binding capacity for a purified Lectin can also be used to optimize a media during development.

In general, the static binding capacity may be can be calculated as follows. A media sample of volume VR is incubated with a solution of purified Lectin of known concentration C1 and known volume VM (HP Lectin in case of blood group A antigen ligand media and GSI-B4 Lectin in case of blood group B antigen ligand media); a supernatant is obtained and the concentration of Lectin (HP or GSI-B4) C2 is measured in the supernatant; the static binding capacity is then calculated using the following equation.

$$\frac{[C1 - C2] \times VM}{VR}$$

The term "dynamic binding capacity" is defined as the amount of a protein that is bound by a chromatography column under flow conditions at the point when the concentration of the protein solution exiting the chromatography column reaches a certain concentration, typically a predetermined percentage of the starting concentration. In practice, this tends to be about 10% of the starting concentration. This mass of protein is then divided by the volume of media in the chromatography column.

The dynamic binding capacity of a particular chromatography media is generally influenced by the composition of the protein solution including one or more of the following factors, e.g., concentration of the protein, concentration of other components in the solution (salts, organic molecules, buffers), the solution pH, and conductivity. The dynamic binding capacity may also be influenced by the temperature at which the column is loaded and by the flow-rate at which the protein solution is loaded onto the column. Decreasing the flow-rate of the protein solution into the chromatography column increases the dynamic binding capacity that is measured. Conversely, increasing the flow-rate of the protein solution into the chromatography column decreases the dynamic binding capacity that is measured. The dynamic binding capacity should not exceed the static binding capacity since the dynamic capacity of a chromatography media is limited by the overall rate of mass transfer.

The term "supernatant" is defined as liquid which is above the settled chromatography media. Supernatant solution may be obtained by allowing the chromatography media in a slurry to settle to the bottom of a container or a column. The settling process can be accelerated by subjecting the slurry of chromatography media to centrifugation or by vibration. The supernatant solution can then be separated from the chromatography media by transferring via a pipetting, syringe, or pump to a separate container. Further, a supernatant may also be obtained by filtering a slurry of chromatography media through a membrane or porous material.

The term "sample" is defined as the solution containing at least one target protein (e.g., anti-A or anti-B antibody in this case) intended to be bound to a chromatography media, as described herein. In some embodiments, the target protein is an antibody or an immunoglobulin. In some embodiments, the immunoglobulin is a blood group A antigen antibody (i.e., anti-A antibody). In other embodiments, the immunoglobulin is a blood group B antigen antibody (i.e., anti-B antibody). Examples of samples include but are not limited to, blood, plasma, plasma derivatives, blood products, intravenous immunoglobulins feed (IVIG).

The term "IgG," "immunoglobulin," "Ig" or "antibody" (used interchangeably herein) refers to a protein having a basic four-polypeptide chain structure consisting of two heavy and two light chains, said chains being stabilized, for example, by interchain disulfide bonds, which has the ability to specifically bind antigen. The term "single-chain immunoglobulin" or "single-chain antibody" (used interchangeably herein) refers to a protein having a two-polypeptide chain structure consisting of a heavy and a light chain, said chains being stabilized, for example, by interchain peptide linkers, which has the ability to specifically bind antigen. The term "domain" refers to a globular region of a heavy or light chain polypeptide comprising peptide loops (e.g., comprising 3 to 4 peptide loops) stabilized, for example, by β-pleated sheet and/or intrachain disulfide bond. Domains are further referred to herein as "constant" or "variable", based on the relative lack of sequence variation within the domains of various class members in the case of a "constant" domain, or the significant variation within the domains of various class members in the case of a "variable" domain. Antibody or polypeptide "domains" are often referred to interchangeably in the art as antibody or polypeptide "regions". The "constant" domains of antibody light chains are referred to interchangeably as "light chain constant regions", "light chain constant domains", "CL" regions or "CL" domains. The "constant" domains of antibody heavy chains are referred to interchangeably as "heavy chain constant regions", "heavy chain constant domains", "CH" regions or "CH" domains. The "variable" domains of antibody light chains are referred to interchangeably as "light chain variable regions", "light chain variable domains", "VL" regions or "VL" domains. The "variable" domains of antibody heavy chains are referred to interchangeably as "heavy chain variable regions", "heavy chain variable domains", "VH" regions or "VH" domains.

Immunoglobulins or antibodies may be monoclonal or polyclonal and may exist in monomeric or polymeric form.

The term "chromatography" as used herein, refers to a dynamic separation technique which separates or removes a molecule (e.g., anti-A and/or anti-B antibodies in this case) from other molecules in a sample. Typically, in a chromatography method, a mobile phase (liquid or gas) transports a sample containing the molecule to be separated or removed through a stationary phase (normally solid) medium (e.g., a chromatography media). Differences in partition or affinity to the stationary phase separate the molecule from other components of the sample.

The term "affinity chromatography," as used herein, refers to a mode of chromatography where a molecule to be separated or removed (e.g., anti-A and/or anti-B antibodies) is isolated by its interaction with another molecule (e.g., a blood group A antigen ligand or blood group B antigen ligand immobilized onto a solid support) which specifically interacts with the molecule to be separated or removed. A media used in affinity chromatography is referred to as an affinity chromatography media.

The term "media" or "chromatography media," as used interchangeably herein, refers to a solid support having a blood group A antigen ligand and/or blood group B antigen ligand immobilized thereon.

The methods described herein can be used for assessing quality of any chromatography media which is suitable for removing anti-A and/or anti-B antibodies, including those described in U.S. Provisional Patent Application Nos. 62/215,431, 62/215,401, filed on Sep. 8, 2015.

In the embodiments described herein, a purified Lectin solution is used to evaluate the binding capacity of a chromatography media including a blood group A antigen ligand or blood group B antigen ligand attached to a solid support. In other words, specific purified Lectin molecules are used as a model molecules to investigate the quality of a chromatography media suitable for removing anti-A or anti-B antibodies.

The terms "anti-A" or "anti-A antibodies" refer to antibodies which bind blood group A antigens found on the surface of cells in individuals that have blood group type A or blood group type AB. Accordingly, it is desirable to remove such antibodies in blood derived samples (e.g., blood, blood products, plasma, plasma derivatives or an IVIG feed).

The terms "anti-B" or "anti-B antibodies" refer to antibodies which bind blood group B antigens found on the surface of cells in individuals that have blood group type B or blood group type AB. Accordingly, it is desirable to remove such antibodies in blood derived samples (e.g., blood, blood products, plasma, plasma derivatives or an IVIG feed).

The term "quality of a media," as used herein, refers to the ability of a chromatography media to selectively remove an undesirable entity (e.g., anti-A or anti-B antibodies) from a sample (e.g., blood, blood products, plasma, plasma derivatives or an IVIG feed). The methods provided herein are especially useful to evaluate and/or monitor the relative quality of different media (e.g., different batches of the same type of media or same type of media from different sources or media samples or prototypes obtained during development or manufacture process) by measuring their binding capacity for a specific purified Lectin molecule. In other words, the relative binding capacities of different batches of same type of media or media obtained from different sources for a purified Lectin (i.e., HP Lectin in case of a blood group A antigen ligand containing media and GSI-B4 Lectin in case of a blood group B antigen ligand containing media) is indicative of the ability of the media to selectively remove anti-A or anti-B antibodies (i.e., relative quality of the media or media samples). Accordingly, the binding capacity of a media for particular purified Lectin molecule can be used to discern the overall quality of the media relative to other batches of the same media or the quality of the same media over time, e.g., during manufacture, use, cleaning and sanitization.

Therefore, a batch of media designed to remove anti-A antibodies which has lower binding capacity for a purified HP Lectin than a previously manufactured batch of that same type of media would be of a poorer quality compared to the previous batch, as it would be expected to remove a lower percentage of anti-A antibodies from a sample. Conversely, a batch of media designed to remove anti-A antibodies which has higher binding capacity for a purified HP Lectin than a previously manufactured batch of that same type of media would be of a better quality relative to the previous batch, as it would be expected to remove a higher percentage of anti-A antibodies from a sample. Similarly, a batch of media which has lower binding capacity for a purified GSI-B4 Lectin than a previously manufactured batch of that same type of media would be of a poorer quality relative to the previous batch, as it would be expected to remove a lower percentage of anti-B antibodies from a sample. Conversely, a media which has higher binding capacity for a purified GSI-B4 Lectin than a previously manufactured batch of that same type of media would be of a better quality than the previous batch, as it would be expected to remove a higher percentage of anti-B antibodies from a sample.

There is generally a need to monitor the quality of chromatography media during its lifetime to ensure that the media retains its ability to remove a desirable percentage of anti-A antibodies or anti-B antibodies from a sample. For example, the quality of the chromatography media may be adversely affected after repeated use, e.g, following exposure to harsh cleaning and/or sanitization conditions, reducing its ability to remove a desirable percentage of anti-A antibodies or anti-B antibodies from a sample. The quality of a batch of media designed to remove anti-A or anti-B antibodies can be monitored by measuring its binding capacity for a purified Lectin, HP and GSI-B4, respectively, before and after the media has been repeatedly used or exposed to harsh cleaning and/or sanitization conditions. If the binding capacity of the media for a purified Lectin has been reduced relative to the previous time it was measured, this would indicate that the media would now remove a lower percentage of anti-A or anti-B antibodies.

Accordingly, the methods described herein are useful for assessing quality of a chromatography media for anti-A or anti-B removal, over time, as well as comparing the quality of two separate batches of media.

Further, the methods described herein may also be used for optimization of a media during manufacture or development. In other words, a prototype media can be evaluated for its ability to remove anti-A or anti-B antibodies, as the case maybe, simply by determining its binding capacity for a purified Lectin, and the media can be further improved or optimized, if necessary, based on its binding capacity for a purified Lectin. For example, once a prototype media is made, the quality of that media can be assessed using the methods described herein, to determine whether it needs further optimization or modifications. This way, various iterations of the media can be easily evaluated for quality during development, leading to the final version of the media.

Additionally, the methods described herein are also useful for differentiating between blood group A antigen ligand media and blood group B antigen ligand media. It is easy for an operator or an end user to mistake the identity of the two media during manufacture and also when used as the two types of media are often manufactured and also stored at the same location and appear virtually identical upon visual inspection. The methods described herein provide a way to distinguish between these two types of media, i.e., when it is unknown whether the media binds anti-A antibodies or anti-B antibodies. For example, the binding capacity of a media of unknown identity (i.e., whether it contains blood group A antigen ligands or blood group B antigen ligands) can be evaluated for a purified HP Lectin and separately for purified GSI-B4 Lectin. An unknown media having blood group A antigen ligands will have a significant binding capacity for purified monoclonal HP Lectin and will have a relatively low or negligible binding capacity for purified GSI-B4 Lectin. An unknown media having blood group B antigens will have a significant binding capacity for purified GSI-B4 Lectin and will have a relatively low or negligible binding capacity for purified HP Lectin.

In some embodiments, the binding capacity of an unknown media for HP or GSI-B4 Lectin can be compared to the binding capacity of a known media of the same type for the Lectins (e.g., from a different batch) to determine whether it includes blood group A antigen ligands or blood group B antigen ligands.

II. Exemplary Blood Group Antigen Media

The methods described herein are useful for assessing the quality of media which binds either blood group A antigen antibodies or blood group B antigen antibodies.

The methods described herein may be used for evaluating any commercially available media or media being developed, which is known to bind blood group A antigen antibodies or blood group B antigen antibodies. Further, the methods described herein may also be used for differentiating between types of media, in the event it is unknown whether the media binds blood group A antigen antibody or blood group B antigen antibody.

Examples of media which may currently be commercially available or has been commercially available at one time include, e.g., the Glycosorb ABO A-column and B column offered by Glycorex Transplantation AB (Solvegatan 41, 223 70 Lund, Sweden); the blood group A trisaccharide Sepharose-4B-AFF201, blood group A trisaccharide Sepharose-FF-AFF101, blood group B trisaccharide Sepharose-4B-AFF202, and Blood group B trisaccharide Sepharose-FF-AFF102, offered by Dextra Laboratories Ltd (Science and Technology Centre, Earley Gate, Whiteknights Road, Reading, RG6 6BZ, United Kingdom); the Synsorb A and B media, offered by Chembiomed Ltd (Edmonton, Alberta, Canada); and the Allotran A and B media offered by Lectinity Holding, Inc. (Moscow, Russia).

In general, any media may be evaluated using the methods described herein, which includes a ligand (typically an oligosaccharide based ligand) corresponding to an epitope of blood group type A antigen or blood group type B antigen attached directly or indirectly (via a linker or a spacer) to a solid support. Exemplary media can also be found in U.S. Provisional Patent Application No. 62/215,401, filed on Sep. 8, 2015.

Exemplary oligosaccharide based ligands are shown below. The abbreviations used in the structure are defined as follows: Gal=D-galactose, Fuc=L-fucose, GalNAc=N-acetyl-D-galactosamine, GlcNAc=N-acetyl-D-glucosamine, R=the linkage from the ligand to the solid support, although linkages at other positions on the ligand structure may also be used.

Examples of blood group type A antigen ligands include, but are not limited to, molecules that having the following structures: trisaccharide antigen A (GalNAcα1,3[Fucα1,2]Galβ-R), tetrasaccharide antigen A Type 1 (GalNAcα1,3[Fucα1,2]Galβ1,3GlcNAcβ1-R), tetrasaccharide antigen A Type 2 (GalNAcα1,3[Fucα1,2]Galβ1,4GlcNAcβ1-R), tetrasaccharide antigen A Type 3 (GalNAcα1,3[Fucα1,2]Galβ1,3GalNAcα1-R), and tetrasaccharide antigen A Type 4 (GalNAcα1,3[Fucα1,2]Galβ1,3GalNAcβ1-R).

Examples of blood group type B antigen ligands include molecules that having the following structures: trisaccharide antigen B (Galα1,3[Fucα1,2]Galβ-R), tetrasaccharide antigen B Type 1 (Galα1,3[Fucα1,2]Galβ1,3GlcNAcβ1-R), tetrasaccharide antigen B Type 2 (Galα1,3[Fucα1,2]Galβ1,4GlcNAcβ1-R), tetrasaccharide antigen B Type 3 (Galα1,3[Fucα1,2]Galβ1,3GalNAcα1-R), and tetrasaccharide antigen B Type 4 (Galα1,3[Fucα1,2]Galβ1,3GalNAcβ1-R).

One or more of the above-mentioned ligands may be attached to a suitable solid support, thereby resulting in a chromatography media which is suitable for removing blood group A and/or blood group B antigen antibodies.

Examples of solid supports include, but are not limited to, alumina, silica, celite, ceramics, metal oxides, porous glass, controlled pore glass, carbohydrate polymers, polysaccharides, agarose, sepharose, sephadex, dextran, cellulose, starch, chitin, zeolites, synthetic polymers, polyvinyl ether, polyethylene, polypropylene, polystyrene, nylons, polyacrylates, polymethacrylates, polyacrylamides, polymaleic anhydride, membranes, hollow fibers and fibers. In some embodiments, the solid support is a polymeric solid support and comprises a polymer selected from the group consisting of polyvinylether, polyvinylalcohol, polymethacrylate, polyacrylate, polystyrene, polyacrylamide, polymethacrylamide and polycarbonate. In a particular embodiment, the solid support is a polyvinylether based solid support. In some embodiments, the solid support is in bead form (e.g., a polyvinyl ether based bead).

It is possible to employ a myriad of functional groups to facilitate attachment of a ligand to a solid support. The non-limiting examples of such functional groups include amine, thiol, furan, maleimide, epoxy, aldehyde, alkene, alkyne, azide, azlactone, carboxyl, activated esters, triazine, and sulfonyl chloride. In a particular embodiment, an amine group is used as a functional group.

The solid support may also be modified and/or activated to include one or more functional groups mentioned above that facilitate immobilization of a suitable ligand or ligands to the support. In a particular embodiment, a carboxyl and aldehyde groups are used as the functional groups.

III. Assays for Measuring Binding Capacity

The methods described herein are useful for assessing the relative quality of media (e.g., during or after a manufacturing process or after use) which binds or is expected to bind blood group A antigen antibodies or blood group B antigen antibodies in a sample, e.g., blood, a blood product, plasma, plasma derivatives or an IVIG feed. The methods described herein, rely, at least in part, on the measurement of the binding capacity of media for a purified Lectin molecule in order to assess the relative quality of media, either over time or when comparing two different batches of a media or media from different sources. Accordingly, the methods described herein may be used to differentiate between the different batches of the same type of media or the same batch of media over its lifetime of use or even media from different sources. In general, the binding capacity of a media for a particular molecule (e.g., Lectin) can be measured as follows. A solution containing the molecule is contacted with a suitable media under appropriate conditions and for a period of time suitable to facilitate binding of the molecule to the media. Thereafter, the molecule that is bound to the media is separated from the remaining sample solution and the concentration of the molecule in the remaining sample solution (i.e., concentration of unbound molecule) is measured. The concentration of the molecule in solution can be determined by several different methods known in the art. For example, the absorbance of the solution can be measured at a particular wavelength and the concentration of the molecule can be calculated in combination with the extinction coefficient of the molecule (e.g., a protein) at that wavelength. Fluorescence, UV, or Raman absorbance can be measured to determine the protein concentration. In addition, the concentration of a molecule in solution can also be determine by analytical chromatography. The intensity of the detection is then correlated to the concentration of the molecule.

In the embodiments described herein, the binding capacity of a blood group type A ligand media or a blood group type B ligand media for a purified HP Lectin or a GSI-B4 Lectin, respectively, is measured, which is then indicative of how that media may perform for the actual removal of anti-A or anti-B antibodies, as the case may be.

Embodiments are further illustrated by the following examples which should not be construed as limiting. The contents of all references, patents and published patent applications cited throughout this application, as well as the Figures, are incorporated herein by reference.

EXAMPLES

Example 1

Figure 1:
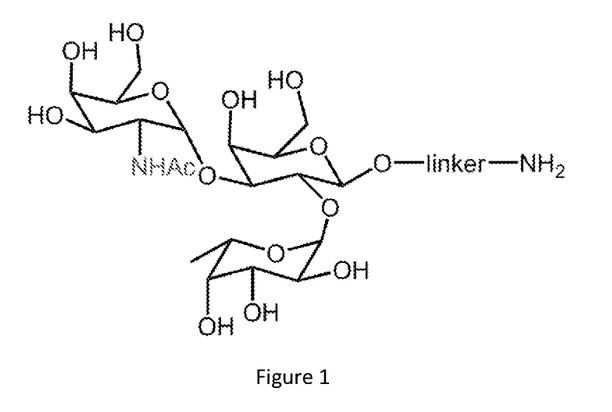
FIG. 1 is a representative oligosaccharide ligand, which binds anti-A antigen antibodies.

Synthesis of Blood Group a Antigen Trisaccharide Ligand Containing Chromatography Media This is an exemplary method which may be used for manufacturing a blood group A antigen ligand media. Blood group A antigen trisaccharide (TriA) ligand containing chromatography media was synthesized by immobilizing TriA ligands onto proprietary polyvinyl ether based beads (i.e., the solid support used herein). The specific structure of the TriA ligand is depicted in FIG. 1. The TriA ligand, in this case, also includes a linker with an amine group, which is used for immobilization onto the base beads. The beads are activated to include a reactive group such as, e.g., an epoxy, a carboxyl or an aldehyde group, which is capable of reacting with an amine group on the ligand. The TriA ligand is then immobilized onto the beads by a coupling reaction with the primary amine (—NH2) group.

Example 2

Figure 2:
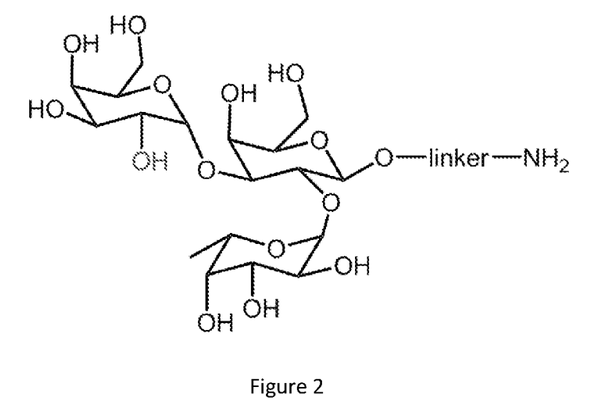
FIG. 2 is a representative oligosaccharide ligand, which binds anti-B antigen antibodies.

Synthesis of Blood Group B Antigen Trisaccharide Ligand Containing Chromatography Media In another experiment, a blood group B antigen ligand media was made as follows. Blood group B antigen trisaccharide (TriB) ligand containing chromatography media was synthesized by immobilizing TriB ligands onto proprietary polyvinyl ether based beads (i.e., the solid support used herein). The specific structure of the TriB ligand is depicted in FIG. 2. The TriB ligand, in this case, also includes a linker with an amine group, which is used for immobilization onto the beads. As in case of the TriA ligand above, the beads are activated to include a reactive group such as, e.g., an epoxy, a carboxyl or an aldehyde group, which is capable of reacting with an amine group on the ligand. The TriB ligand is then immobilized onto the base beads by a coupling reaction with the primary amine (—NH2) group.

Example 3

Capacity of Blood Group a Antigen Trisaccharide Ligand Media for *Helix pomatia* (HP) Lectin as an Indicator of Media Quality This is a representative example demonstrating that the capacity of blood group A antigen trisaccharide (TriA) ligand media for purified HP Lectin (Sigma Aldrich, Cat # L3382) can be used to evaluate the quality of the media, e.g., during and after manufacturing. The concentration of a TriA ligands was varied during the coupling reaction with the support solid. The media should therefore have differing amount of the TriA ligands, which simulates the type of variation that might occur during the media manufacturing process. The static binding capacity of the various TriA ligand media for the HP Lectin was subsequently measured. This value was compared with the percentage of anti-A IgG antibody removal from an IVIG feed.

A set of 2.0 mL microcentrifuge tubes were filled with 0.35 mL of 10 mM PBS buffer or 0.50 mL of 10 mM PBS buffer for the controls. Subsequently, 0.15 mL of a 10% suspension of the media (15 µL media volume) in 10 mM PBS buffer was added to the microcentrifuge tubes, except for the controls, followed by the addition of 0.6 mL of a 1 mg/mL HP Lectin solution in PBS buffer. Additional 0.4 ml of PBS was added to all the tubes. The tubes were allowed to rotate for 4 hours at room temperature. Subsequently, the microcentrifuge tubes were subjected to centrifugation and the resulting supernatant was transferred into centrifugal filtration devices with a 0.22 micron membrane. The devices were subjected to centrifugation and then the absorbance of the filtrate was measured at 280 nm. The solution absorbance of each sample was then used to calculate the media's static binding capacity for HP Lectin. The HP Lectin static binding capacity was compared with the percentage removal of anti-A IgG antibodies from an IVIG feed under static binding conditions.

For measuring IgG removal, blood group A antigen polyclonal IgG antibody (anti-A) level in a representative IVIG feed was determined by an established flow cytometry method (Christensson, M. et al, Transfusion, 1996, 36, 500-505). Type A red blood cells were incubated with the representative IVIG feed for a pre-determined time, followed by extensive washes. The cells were then stained with fluorescence-labeled anti-human IgG (Alexa Fluor® 488 AffiniPure F(ab')$_2$ Fragment Goat Anti-Human IgG (H+L), part number: 109-546-088, Jackson ImmunoResearch, West Grove, Pa., USA), and subjected to Flow Cytometry (Guava 5HT, EMD Millipore). Net mean fluorescence intensity (MFI) values were used to compare anti-A polyclonal IgG concentrations in the feed before and after contact with the blood group A trisaccharide antigen ligand media which is synthesized in Example 1.

In order to simulate the variation in the capacity of the media typically observed during manufacturing and also between batches, samples were synthesized by varying the trisaccharide ligand loading in the synthesis step. The ligand loading for the samples listed in Table 2 were in the order of: Media #1<Media #2<Media #3. Solid support alone was used as a control, which in this case was polyether based beads. As summarized in Table 2 below, this experiment demonstrates that the static binding capacity of the various TriA ligand media for HP Lectin correlates with the percentage removal of anti-A antibodies from an IVIG feed under static binding conditions. It was found that the TriA ligand media with higher capacities for HP Lectin removed more anti-A IgG antibodies from an IVIG feed. It was also found that the TriA ligand media with lower static binding capacities for HP Lectin removed less anti-A IgG antibodies from an IVIG feed.

It was somewhat unexpected to find that the static binding capacity of TriA ligand media for HP Lectin correlates with the percentage removal of anti-A IgG antibodies, as the two molecules, e.g., IgG and HP Lectin are very different types of molecules.

TABLE 2

Binding capacity of three different TriA media and control for HP Lectin and the percentage removal of anti-A antibodies.

| | HP Lectin static binding capacity (mg/ml) | percentage removal of anti-A IgG from an IVIG feed |
|---|---|---|
| TriA media #1 | 4.0 | 81% |
| TriA media #2 | 5.7 | 82% |
| TriA media #3 | 7.6 | 84% |
| Control | <0.01 | None |

Example 4

Binding Capacity of Blood Group B Antigen Trisaccharide Ligand Media for *Griffonia simplicifolia*-IsoLectin B4 (GSI-B4) Lectin as an Indicator of Media Quality This is a representative example demonstrating that the capacity of blood group B antigen trisaccharide (TriB) ligand media for GSI-B4 Lectin (Sigma Aldrich; Cat # L3019) can be used to evaluate the quality of the media, e.g., during and after manufacturing. The concentration of a TriB ligands was varied during the coupling reaction with the solid support to simulate the variation seen during manufacturing. The static binding capacity of the various TriB ligand media for GSI-B4 Lectin was measured and compared with the percentage removal of anti-B IgG antibodies from an IVIG feed. If the two values are found to correlate, then measuring the TriB ligand media's capacity for GSI-B4 Lectin can be used to evaluate its ability to remove anti-B IgG antibodies from an IVIG feed. Product specifications for TriB media's quality can subsequently be established based on its capacity for the GSI-B4 Lectin.

A set of 2.0 mL microcentrifuge tubes were filled with 0.35 mL of PBS buffer or 0.50 mL of PBS buffer for the controls. Subsequently, 0.15 mL of a 10% suspension of the media 15 μL media volume) in 10 mM PBS buffer was added to the microcentrifuge tubes, except for the controls, followed by the addition of 0.6 mL of a 1 mg/mL GSI-B4 Lectin solution in PBS buffer. Additional 0.4 ml of PBS was added to all the tubes. The tubes were allowed to rotate for 16 hours at room temperature. Then the microcentrifuge tubes were placed into a centrifuge and then the supernatant was transferred into a centrifugal filtration devices with a 0.22 micron membrane. The devices were subjected to centrifuge and then the absorbance of the filtrate was measured at 280 nm. The solution absorbance of each sample was then used to calculate the media's static binding capacity for GSI-B4 Lectin. The GSI-B4 Lectin static binding capacity was then compared with the percentage removal obtained when the same media was used to remove anti-B IgG antibodies from an IVIG feed under static binding conditions.

For measuring IgG removal, blood group B antigen polyclonal IgG antibody (anti-B) level in a representative IVIG feed was determined by an established flow cytometry method (Christensson, M. et al, Transfusion, 1996, 36, 500-505). Type B red blood cells were incubated with the representative IVIG feed for a pre-determined time, followed by extensive washes. The cells were then stained with fluorescence-labeled anti-human IgG as above, and subjected to Flow Cytometry (Guava 5HT, EMD Millipore). Net mean fluorescence intensity (MFI) values were used to compare anti-B polyclonal IgG concentrations in the feed before and after contact with the blood group B trisaccharide antigen ligand media which is synthesized in Example 2.

In order to simulate the variation in the capacity of the media to remove the anti-B IgG antibodies, samples were synthesized by varying the trisaccharide ligand loading in the synthesis step. The ligand loading for the samples listed in Table 3 were in the order of: Media #4<Media #5<Media #6. Solid support alone was used as a control, which in this case was polyether based beads. As summarized in Table 3 below, this experiment demonstrates that the static binding capacity of the various TriB ligand media for GSI-B4 Lectin correlates with the percentage removal of anti-B IgG antibodies from an IVIG feed under static binding conditions. It was found that the TriB ligand media with higher capacities for GSI-B4 Lectin removed more anti-B IgG antibodies from an IVIG feed. It was also found that the TriB ligand media with lower static binding capacities for GSI-B4 Lectin removed less anti-B IgG antibodies from an IVIG feed.

It was somewhat unexpected to find that the static binding capacity of TriB ligand media for GSI-B4 Lectin correlates with the percentage removal of anti-B IgG antibodies, as the two molecules, e.g., IgG and GSI-B4 Lectin are very different types of molecules.

TABLE 3

Binding capacity of three different TriB media and control for GSI-B4 and percentage removal of anti-B IgG from an IVIG feed.

| | GSI-B4 static binding capacity (mg/ml) | percentage removal of anti-B IgG removed from an IVIG feed |
|---|---|---|
| TriB Media #4 | 0.19 | 74% |
| TriB Media #5 | 0.33 | 86% |
| TriB Media #6 | 0.58 | 92% |
| Control | <0.01 | None |

Example 5

A Method to Distinguish Between Blood Group a Antigen Trisaccharide Ligand Media and Blood Group B Antigen Trisaccharide Ligand Media by Measuring the Relative Capacities of the Media for HP and GSI-B4 Lectins This is a representative example demonstrating that the relative capacities of blood group A antigen trisaccharide (TriA) ligand media and blood group B antigen trisaccharide (TriB) ligand media for HP and GSI-B4 Lectins can be used to differentiate between the types of the media.

A set of 2.0 mL microcentrifuge tubes were filled with 0.35 mL of PBS buffer or 0.50 mL of PBS buffer for the controls. Subsequently, 0.15 mL of a 10% suspension of the media (15 media volume) in PBS buffer was added to the microcentrifuge tubes except for the control solutions. 0.6 mL of a 1.0 mg/mL HP Lectin solution in PBS buffer and 0.6 mL of a 1.0 mg/mL GSI-B4 Lectin solution in PBS buffer was added to all the tubes. Additional 0.4 ml of PBS buffer was added to the centrifuge tubes. The tubes were then allowed to rotate for 4 hours and 16 hours at room temperature for HP and GSI-B4 Lectins, respectively. The microcentrifuge tubes were placed into a centrifuge and the resulting supernatant was transferred into a centrifugal filtration devices with a 0.22 micron membrane. The devices were subjected to centrifugation and the absorbance of the filtrate was measured at 280 nm. The solution absorbance of each sample was then used to calculate the media's static binding capacity for HP and GSI-B4 Lectin.

As summarized in Table 4 below, this experiment demonstrates that the relative binding capacities of media for both HP and GSI-B4 Lectins, can be used to differentiate between the types of media. Specifically, it was found that the TriA ligand media had a significant binding capacity for the HP Lectin while almost negligible binding capacity for the GSI-B4 Lectin. Conversely, the TriB ligand media had a significant binding capacity for the GSI-B4 Lectin while it had almost negligible binding capacity for the HP Lectin. Therefore, in instances where the identity of a media sample is unknown and it is not known whether it is suitable for removing anti-A or anti-B antibodies, the binding capacity of the media sample for HP and GSI-B4 Lectins can be measured, as described herein, thereby to determine whether it is suitable for removing anti-A or anti-B antibodies.

TABLE 4

Capacity of TriA ligand media and TriB ligand media for HP and GSI-B4 Lectins.

| | HP Lectin binding capacity (mg/ml) | GSI-B4 Lectin static binding capacity (mg/ml) |
|---|---|---|
| TriA media #A | 7.60 | <0.1 |
| TriB media #B | <0.1 | 0.58 |

Example 6

Capacity of Blood Group A and B Antigen Trisaccharide Ligand Media for *Griffonia simplicifolia* (GS-I) Lectin as an Indicator of Media Quality This is a representative example demonstrating that the capacity of blood group A and B antigen trisaccharide (TriA and TriB) ligand media for GS-I Lectin (Sigma Aldrich; L2380) can be used to evaluate the quality of the media, e.g., during and after manufacturing. The static binding capacity of the various TriA and TriB ligand media for the GS-I is measured. This value is then compared with the percentage of anti-A and anti-B IgG antibody removal from an IVIG feed. If the two values are found to correlate, then measuring the TriA and TriB ligand media's capacity for GS-I Lectin can be used to evaluate its ability to remove anti-A and anti-B IgG antibodies from an IVIG feed. Product specifications for TriA and TriB media's quality can subsequently be established based on its binding capacity for GS-I Lectin.

A set of 2.0 mL microcentrifuge tubes were filled with 0.35 mL of PBS buffer or 0.50 mL of PBS buffer for the controls. Subsequently, 0.15 mL of a 10% suspension of the media (15 media volume) in PBS buffer was added to the microcentrifuge tubes except for the control solutions. 0.6 mL of a 1.0 mg/mL GS-I Lectin solution in PBS buffer was added to all the tubes and an additional 0.4 ml of PBS was added to all the tubes. The tubes were allowed to rotate for 16 hours at room temperature. Then the microcentrifuge tubes were placed into a centrifuge and then the resulting supernatant was transferred into a centrifugal filtration devices with a 0.22 micron membrane. The devices were subjected to centrifugation and the absorbance of the filtrate was measured at 280 nm. The solution absorbance of each sample was then used to calculate the media's static binding capacity for GS-I Lectin. The GS-I Lectin static binding capacity was then compared with the percentage removal of anti-A and anti-B antibodies from an IVIG feed under static binding conditions.

As summarized in Table 5 below, this experiment demonstrates that the static binding capacity of the various TriA and TriB ligand media for GS-I Lectin correlates with the percentage removal of anti-A and anti-B IgG antibodies from an IVIG feed under static binding conditions. It was found that the TriA and TriB ligand media with significant binding capacity for GS-I Lectin also removed significant amounts of anti-A and anti-B IgG antibodies, respectively, from an IVIG feed.

TABLE 5

Binding capacity of TriB media for GS-I correlates with percentage removal of anti-B IgG removed from an IVIG feed.

| | GS-I Lectin static binding capacity (mg/ml) | percentage removal of anti-B IgG removed from an IVIG feed |
|---|---|---|
| TriA media #B1 | 0.33 | 81% |
| TriB media #B2 | 0.81 | 92% |

Example 7

Generating a Mixture of Media Based on Binding Capacities for HP-1 and GSI-B4 Lectins As observed herein, the binding capacity of a blood group A antigen media or a blood group B antigen media to purified HP-1 and GSI-B4 Lectins, respectively, is a good indicia to assess or predict how such media may actually perform for the removal of blood group A antigen antibodies or blood group B antigen antibodies from a sample (e.g., blood, blood product, plasma or an IVIG feed).

The binding capacity measurement for a Lectin may also be used to generate a mixture of such media in the right proportion, which can then be used to remove both blood group A antigen antibodies and blood group B antigen antibodies from a sample in one chromatography step.

This is particularly useful as generally, the amounts of blood group A antigen antibodies and blood group B antigen antibodies tend to vary from sample to sample. Therefore, a mixture of media which may work well for removal of such antibodies from one sample may not work as well in case of another sample.

The methods described herein can be used to design a mixture of media which would work well for a sample, by simply knowing the amounts of anti-A and anti-B antibodies in that sample.

For example, since the binding capacity of a media for HP and GSI-B4 Lectin correlates with the removal of anti-A or anti-B antibodies, respectively, from a sample, once the level or amount of anti-A and anti-B antibodies in a sample is known, a mixture of media can be designed, such that to have a ratio of the blood group A antigen media and a blood group B antigen media, which would be suitable to remove a desired amount of anti-A and/or anti-B antibodies from the sample.

The specification is most thoroughly understood in light of the teachings of the references cited within the specification which are hereby incorporated by reference. The embodiments within the specification provide an illustration of embodiments and should not be construed as limiting in scope. The skilled artisan (practitioner) readily recognizes that many other embodiments are encompassed by this disclosure. All publications and reference materials are incorporated by reference in their entirety. To the extent that the material incorporated by reference contradicts or is inconsistent with the present specification, the present specification will supercede any such material. The citation of any references herein is not an admission that such references are prior art.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the embodiments disclosed herein. Unless otherwise indicated, the term "at least" preceding a series of elements is to be understood to refer to every element in the series. Those skilled in the art will recognize, or be able to ascertain using no more than routine experimentation, many equivalents to the specific embodiments described herein. Such equivalents are intended to be encompassed by the following claims.

Many modifications and variations of the embodiments disclosed herein can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the disclosure being indicated by the following claims.

What is claimed is:

1. Method of comparing quality of two or more affinity chromatography media samples containing blood group A antigen ligands attached to a solid support, the method comprising the steps of:

(a) for each of the media samples, providing a solution of purified HP Lectin of known concentration C1 and volume VM and an affinity chromatography media sample of volume VR;

(b) incubating each chromatography media sample with the solution of (a);

(c) obtaining a supernatent and measuring the concentration C2 of the purified HP Lectin in the supernatant, for each chromatography media sample;

(d) determining the static binding capacity of each chromatography media sample for the purified Lectin, wherein the static binding capacity is measured using the equation $([C1-C2]\times VM)/VR$ wherein the static binding capacities of the media samples correlates with their ability to remove anti-A antibodies from a sample, thereby providing a comparison of the quality of two or more different affinity chromatography media samples; and (e) purifying blood or a blood derived product with a media sample determined by step (d) to provide media capable of selectively removing antibodies.

2. Method of comparing quality of two or more affinity chromatography media samples containing blood group B antigen ligands attached to a solid support, the method comprising the steps of:

(a) for each of the media samples, providing a solution of purified GSI-B4 Lectin of known concentration C1 and volume VM and an affinity chromatography media sample of volume VR;

(b) incubating each chromatography media sample with the solution of (a);

(c) obtaining a supernatent and measuring the concentration C2 of the GSI-B4 Lectin in the supernatant, for each chromatography media sample;

(d) determining the static binding capacity of each chromatography media sample for the purified GSI-B4 Lectin, wherein the static binding capacity is measured using the equation $([C1-C2]\times VM)/VR$ wherein the static binding capacities of the media samples correlates with their ability to remove anti-B antibodies from a sample, thereby providing a comparison of the quality of two or more affinity chromatography media samples; and (e) purifying blood or a blood derived product with a media sample determined by step (d) to provide media capable of selectively removing antibodies.

3. The method of claim 1, wherein the solid support is a porous or non-porous polymeric solid support comprising a polymer selected from the group consisting of polyvinylether, polyvinylalcohol, polymethacrylate, polyacrylate, polystyrene, polyacrylamide, polymethacrylamide and polycarbonate.

4. The method of claim 2, wherein the solid support is a porous or non-porous polymeric solid support comprising a polymer selected from the group consisting of polyvinylether, polyvinylalcohol, polymethacrylate, polyacrylate, polystyrene, polyacrylamide, polymethacrylamide and polycarbonate.

5. The method of claim 1, wherein the solid support is a polyvinylether based porous solid support.

6. The method of claim 2, wherein the solid support is a polyvinylether based porous solid support.

7. The method of claim 5, wherein the polyvinylether based porous solid support is in bead form.

8. The method of claim 6, wherein the polyvinylether based porous solid support is in bead form.

9. The method of claim 1, wherein the binding capacity of the blood group A antigen ligand media for purified HP Lectin correlates with its ability to remove anti-A antibodies from a sample.

10. The method of claim 2, wherein the binding capacity of the blood group B antigen ligand media for purified GSI-B4 Lectin correlates with its ability to remove anti-B antibodies from a sample.

11. The method of claim 1, wherein the two or more affinity chromatography media samples constitute different batches of the same media.

12. The method of claim 2, wherein the two or more affinity chromatography media samples constitute different batches of the same media.

13. The method of claim 1, wherein the different affinity chromatography media samples constitute the same media at different stages of use.

14. The method of claim 2, wherein the different affinity chromatography media samples constitute the same media at different stages of use.

15. The method of claim 11, wherein the sample is selected from the group consisting of blood, blood products, plasma, plasma derivatives and IVIG feed.

16. The method of claim 12, wherein the sample is selected from the group consisting of blood, blood products, plasma, plasma derivatives and IVIG feed.

17. The method of claim 13, wherein the sample is selected from the group consisting of blood, blood products, plasma, plasma derivatives and IVIG feed.

18. The method of claim 14, wherein the sample is selected from the group consisting of blood, blood products, plasma, plasma derivatives and IVIG feed.

19. The method of claim 1, wherein the measurement of concentration comprises determining absorbance at 280 nm.

20. The method of claim 2, wherein the measurement of concentration comprises determining absorbance at 280 nm.

21. A method of assessing quality of a media following exposure to acid or alkaline conditions, wherein the method comprises the steps of:
(a) providing a chromatography media having wither blood group A antigen ligands or blood group B antigen ligands attached to a solid support;
(b) measuring, via absorbance at a particular wavelength, the binding capacity of the unknown media for purified HP Lectin and separately for purified GSI-B4 Lectin; the binding capacity of the media for purified HP Lectin in case of blood group A antigen antibody or for purified GSI-B4 Lectin in case of blood group B antigen antibody;
(c) exposing the media to acid or alkaline conditions for at least 5 hours; and
(d) measuring the binding capacity of the media for purified HP Lectin in case of blood group A antigen antibody or for purified GSI-B4 Lectin in case of blood group B antigen antibody;
wherein a reduction in the binding capacity of media in (d) relative to (b) indicates that the quality of media has decreased following exposure to acid of alkaline conditions.

22. The method of claim 21, wherein a decrease in quality of media comprises a reduction in the ability of media to remove anti-A of anti-B antibodies.

23. Method of determining whether a media comprises blood group A antigen ligands or blood group B antigen ligands, wherein the method comprises the steps of:
(a) providing a media, wherein it is unknown whether the media comprises blood group A antigen ligands or blood group B antigen ligands;
(b) measuring, via absorbance at a particular wavelength, the binding capacity of the unknown media for purified HP Lectin and separately for purified GSI-B4 Lectin; and
(c) comparing the binding capacity of the unknown media for purified HP Lectin and for purified GSI-B4 Lectin, wherein the media is determined to comprise blood group A antigen ligands, if the binding capacity of the media for HP Lectin is greater than the binding capacity for GSI-B4 Lectin, and the media is determined to comprise blood group B antigen ligands if the binding capacity of the media for GSI-B4 Lectin is greater than the binding capacity for HP Lectin.

* * * * *